(12) United States Patent
Lorimer et al.

(10) Patent No.: US 7,550,592 B2
(45) Date of Patent: Jun. 23, 2009

(54) HYDROMORPHONE POLYMORPHS

(75) Inventors: Keith R. Lorimer, West Lafayette, IN (US); Alicia T. Ng, West Lafayette, IN (US)

(73) Assignee: Noramco, Inc., Athens, GA (US)

( * ) Notice: Subject to any disclaimer, the term of this patent is extended or adjusted under 35 U.S.C. 154(b) by 210 days.

(21) Appl. No.: 11/405,286

(22) Filed: Apr. 17, 2006

(65) Prior Publication Data

US 2006/0235039 A1    Oct. 19, 2006

Related U.S. Application Data

(60) Provisional application No. 60/672,275, filed on Apr. 18, 2005.

(51) Int. Cl.
*C07D 489/04* (2006.01)
*C07D 489/02* (2006.01)

(52) U.S. Cl. .................... 546/45; 546/44; 514/282

(58) Field of Classification Search ............ 514/282; 546/45, 44

See application file for complete search history.

(56) References Cited

FOREIGN PATENT DOCUMENTS

| WO | WO 01/34608 | 5/2001 |
| WO | WO 2006/005112 | 1/2006 |

OTHER PUBLICATIONS

Kofler, L., et al., "Zur, Identifizierung von Alkaloiden", Mikrochemie, vol. 33, 1948, pp. 70-103, p. 100.
S.D. Roy and G. L. Flynn, Pharmaceutical Research, 5, (9), 580, 1998.
Material Safety Data Sheet, Purdue Pharma, L.P.
H. Steinmetz, *Chemiker-Zeitung*, 52, 162, 1928.
Gross S. Oberst, J. Lab. Clinical Med, 32, 94, 1947.
Barnes, Sheppard, Bulletin on Narcotics, 6, 27, 1954.
N.B. Eddy, J.G. Reid, J. Pharmacol, 52, 468, 1934.
H. Steinmetz, *Zeitschrift fuer Kristallographie, Kristphysik, Kristllchemie*, 67, 434-9, 1928.
L. Small, S.G. Turnbull, H.M. Fitch, *J. Org. Chem.*, 3, 204, 1938.
Merck Index, 13th Edition, pp. 859-860.
PCT International Application, dated Jul. 31, 2006, for PCT Int'l. Appln. No. PCT/US2006/014533.

*Primary Examiner*—Charanjit S Aulakh
(74) *Attorney, Agent, or Firm*—Mary A. Appolina

(57) ABSTRACT

Hydromorphone hydrochloride forms are disclosed which are useful as analgesic agents either in combination with or as replacements for hydromorphone hydrochloride.

17 Claims, 5 Drawing Sheets

*FIG. 5*

HYDROMORPHONE POLYMORPHS

CROSS-REFERENCE TO RELATED APPLICATIONS

This application claims priority from U.S. Provisional Application Ser. No. 60/672,275, filed Apr. 18, 2005, the contents of which are hereby incorporated by reference in their entirety.

BACKGROUND OF THE INVENTION

Hydromorphone hydrochloride (4,5(alpha)-epoxy-3-hydroxy-17-methylmorphinan-6-one hydrochloride) is a semi synthetic opioid structurally related to morphine. Hydromorphone HCl is well known as an effective analgesic indicated for the relief of moderate to severe pain such as that due to: surgery, cancer, trauma (soft tissue & bone), biliary colic, myocardial infarction, burns and renal colic. It is commercially available from Abbott Laboratories (North Chicago, Ill. 60064) as Dilaudid® in tablets, ampules and multiple dose vials (for parenteral administration), suppositories (for rectal administration) and non-sterile powder (for prescription compounding). For oral administration, tablets in dosage forms of 2 and 4 mg are available.

SUMMARY OF THE INVENTION

The present invention is directed to four novel forms of hydromorphone HCl. These are identified herein as Forms B, C, D and an amorphous form. The known form of hydromorphone HCl is referred to hereinafter as hydromorphone HCl Form A.

DETAILED DESCRIPTION

All four forms are derived directly or indirectly from hydromorphone HCl Form A and are characterized by physical data, most notable by their X-ray powder diffraction ("XRPD") patterns expressed in terms of °2θ and the relative intensities of the X-ray diffraction peaks.

One aspect of the invention is the novel forms of hydromorphone HCl. Another aspect of this invention is processes to make these novel forms. These novel forms of hydromorphone HCl can be used instead of or in combination with hydromorphone HCl Form A for its pharmacological effects. The novel forms may be produced and used as the pure form, or the forms may be produced and used in combination with the other novel forms and/or hydromorphone HCl Form A. Another aspect of the invention is pharmaceutical compositions comprising therapeutically effective amounts of one or more of these novel forms, optionally in combination with hydromorphone HCl Form A, and pharmaceutically acceptable carriers therefor. Another aspect is a method of providing a therapeutic (e.g., analgesic) effect to a mammal, preferably a human, in need thereof which comprises administering to said mammal a therapeutic amount of one or more of a novel form of the invention, optionally in combination with hydromorphone HCl Form A. Hydromorphone HCl Form A, its therapeutic uses and dose ranges, modes of administration, etc. are all well known in the art.

By pure is meant that each form of the invention is about 90-100%, preferably 95-100%, more preferably 98-100% (wt./wt.) pure; e.g. free of other hydromorphone HCl forms, solvents, and/or other undesirable non-hydromorphone HCl impurities. A preferred form of the invention is one that is free of other hydromorphone HCl forms, preferably 98-100% free.

One embodiment of the invention is the forms of hydromorphone HCl made by the processes such as recited in the examples. Another embodiment of the invention is the forms of hydromorphone HCl as identified by the X-ray powder diffraction patterns shown below.

Table I summarizes the prominent peaks of the X-ray powder diffraction ("XRPD") patterns of each hydromorphone HCl form. The relative intensity ("R.I.") of each peak is shown, wherein R.I. is the ratio of the height of each peak compared to the highest peak, which is designated as 100%.

Figure 1:
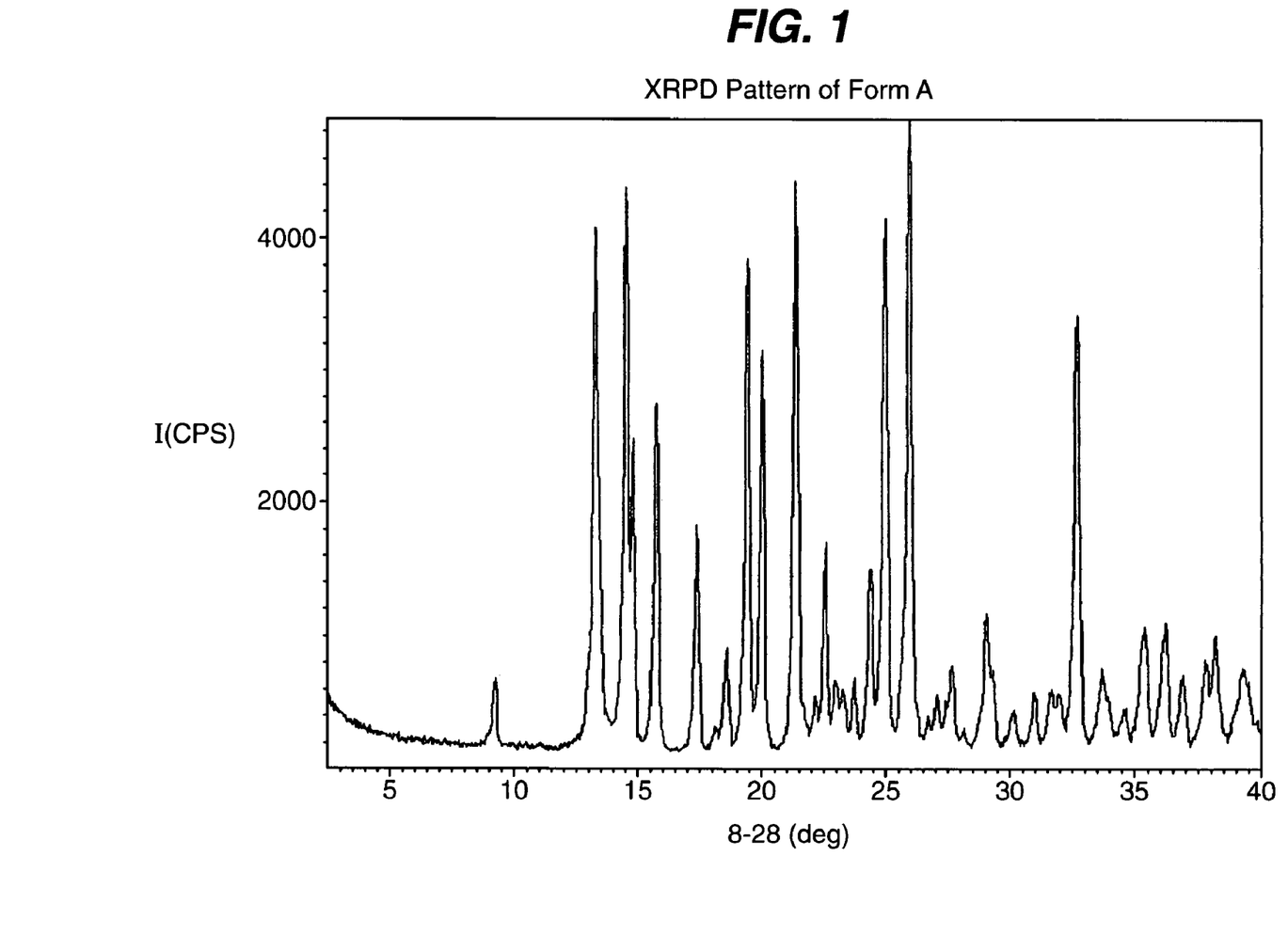
FIG. 1 is an X-ray powder diffraction pattern of hydromorphone HCl Form A expressed in terms of °2θ.
Figure 2:
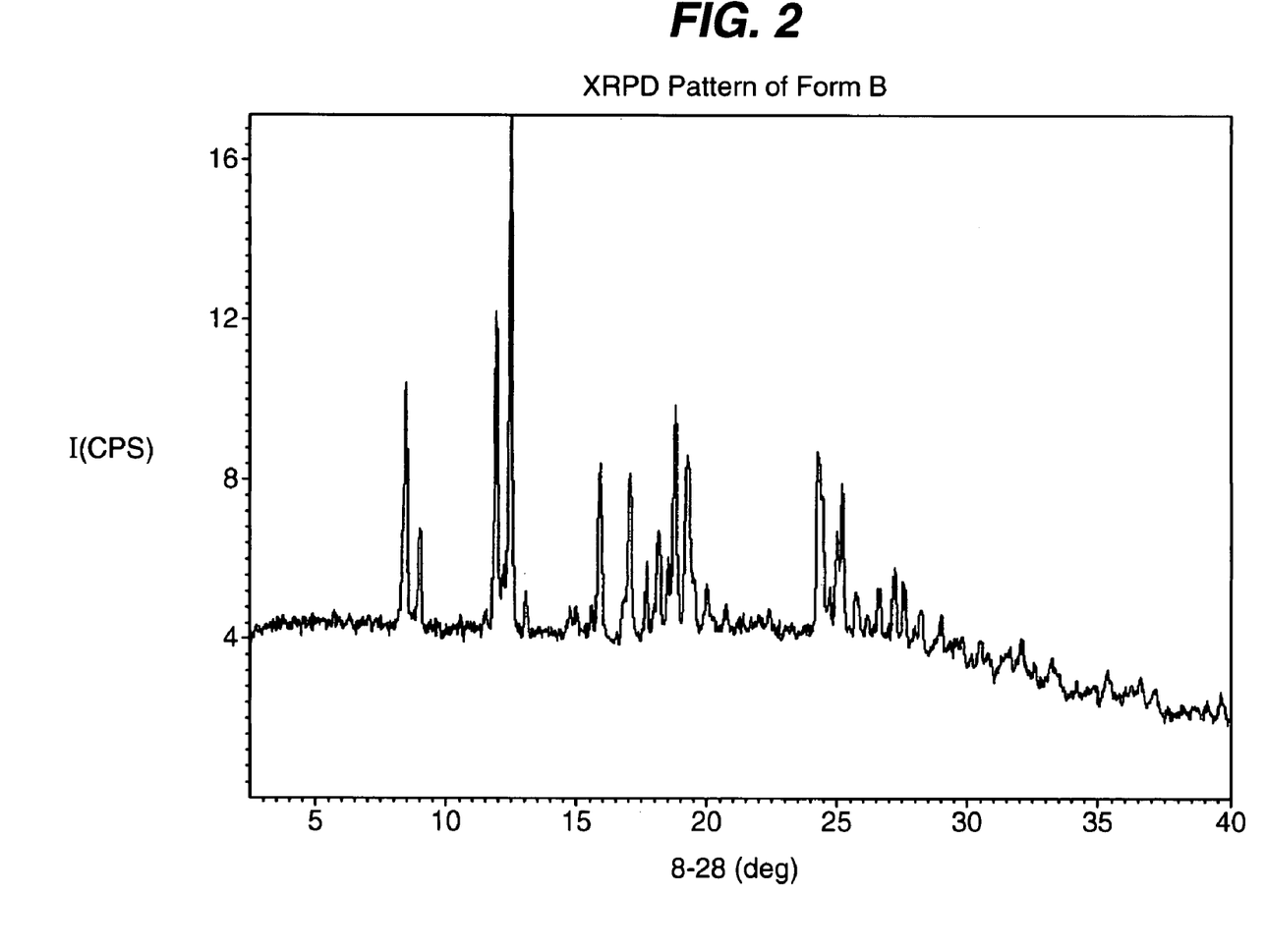
FIG. 2 is an X-ray powder diffraction pattern of hydromorphone HCl Form B expressed in terms of °2θ.
Figure 3:
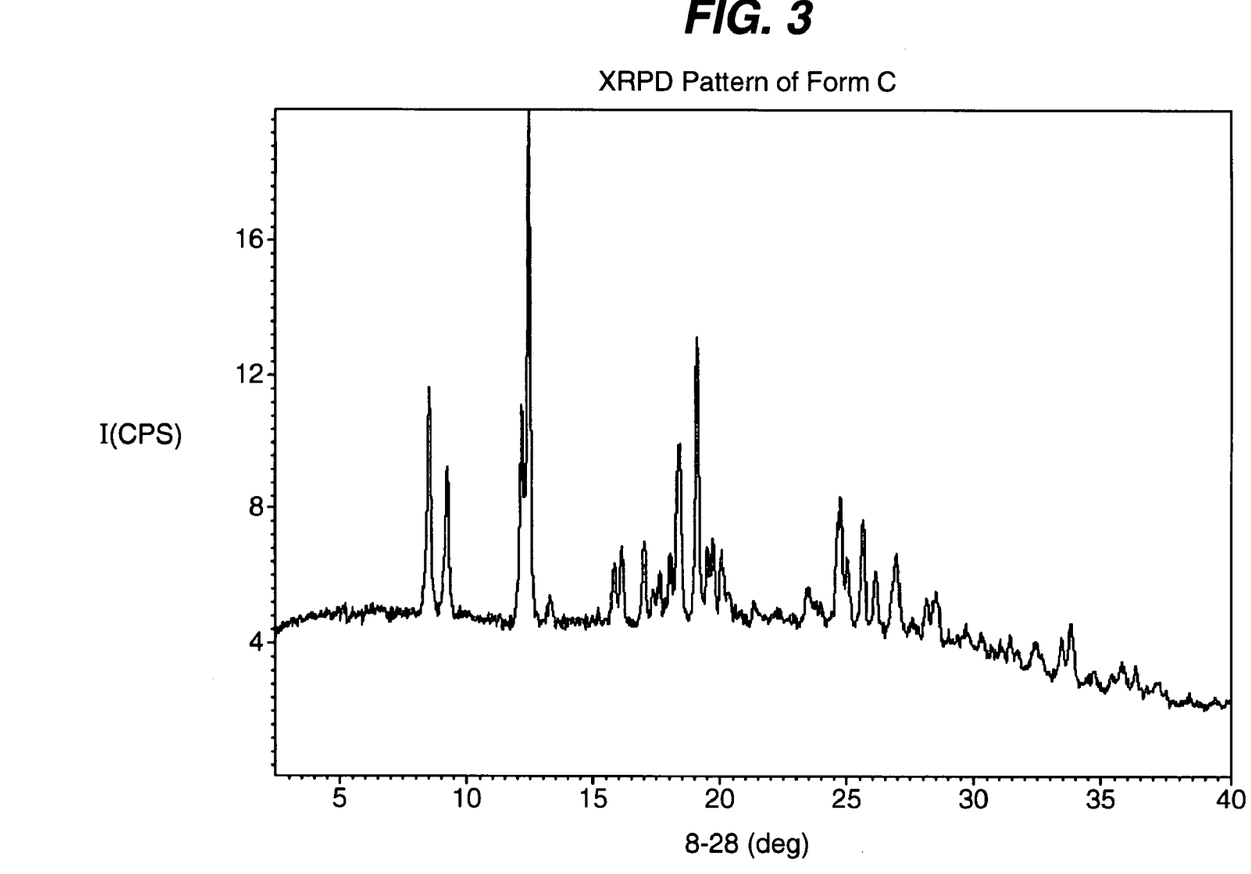
FIG. 3 is an X-ray powder diffraction pattern of hydromorphone HCl Form C expressed in terms of °2θ.
Figure 4:
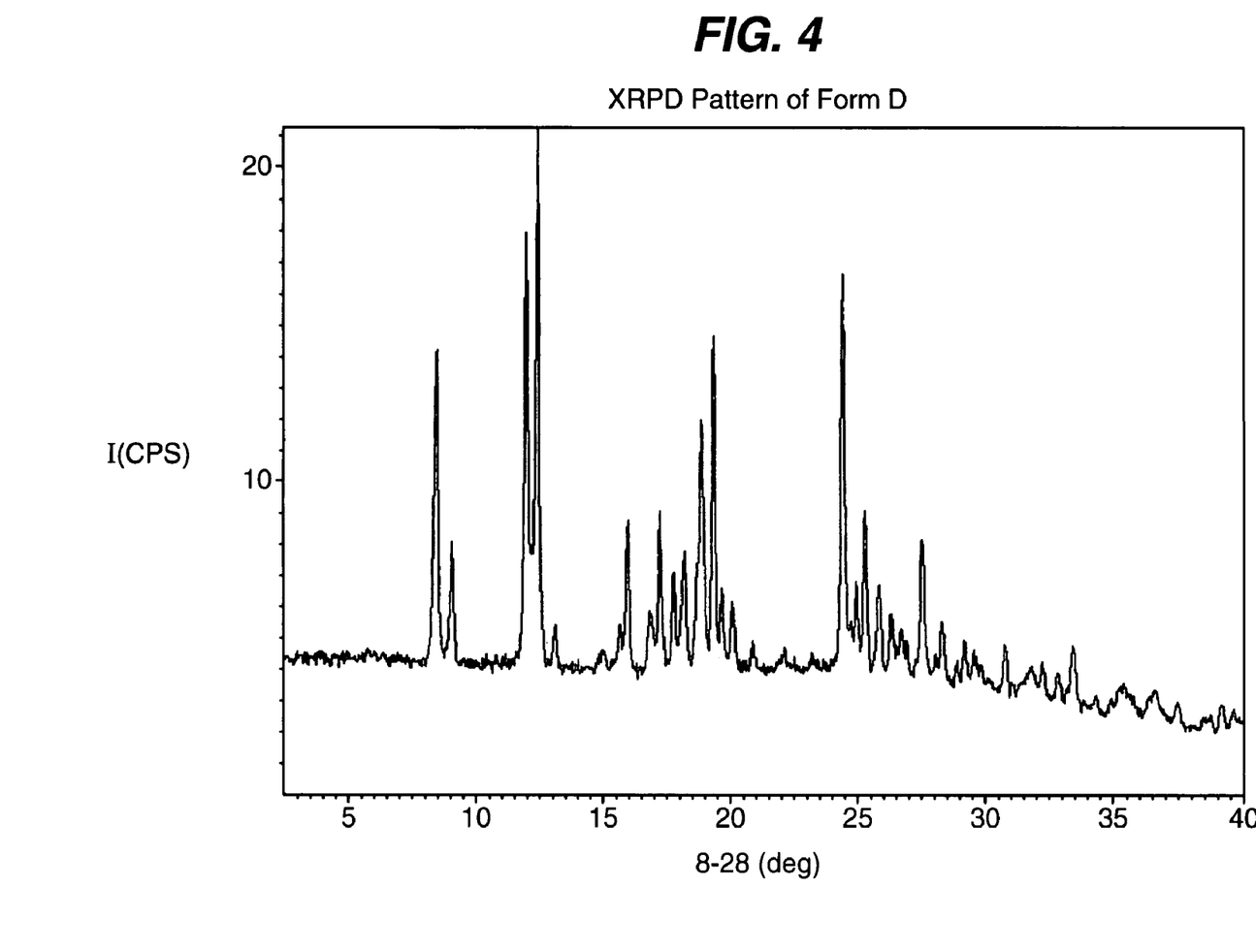
FIG. 4 is an X-ray powder diffraction pattern of hydromorphone HCl Form D expressed in terms of °2θ.
Figure 5:
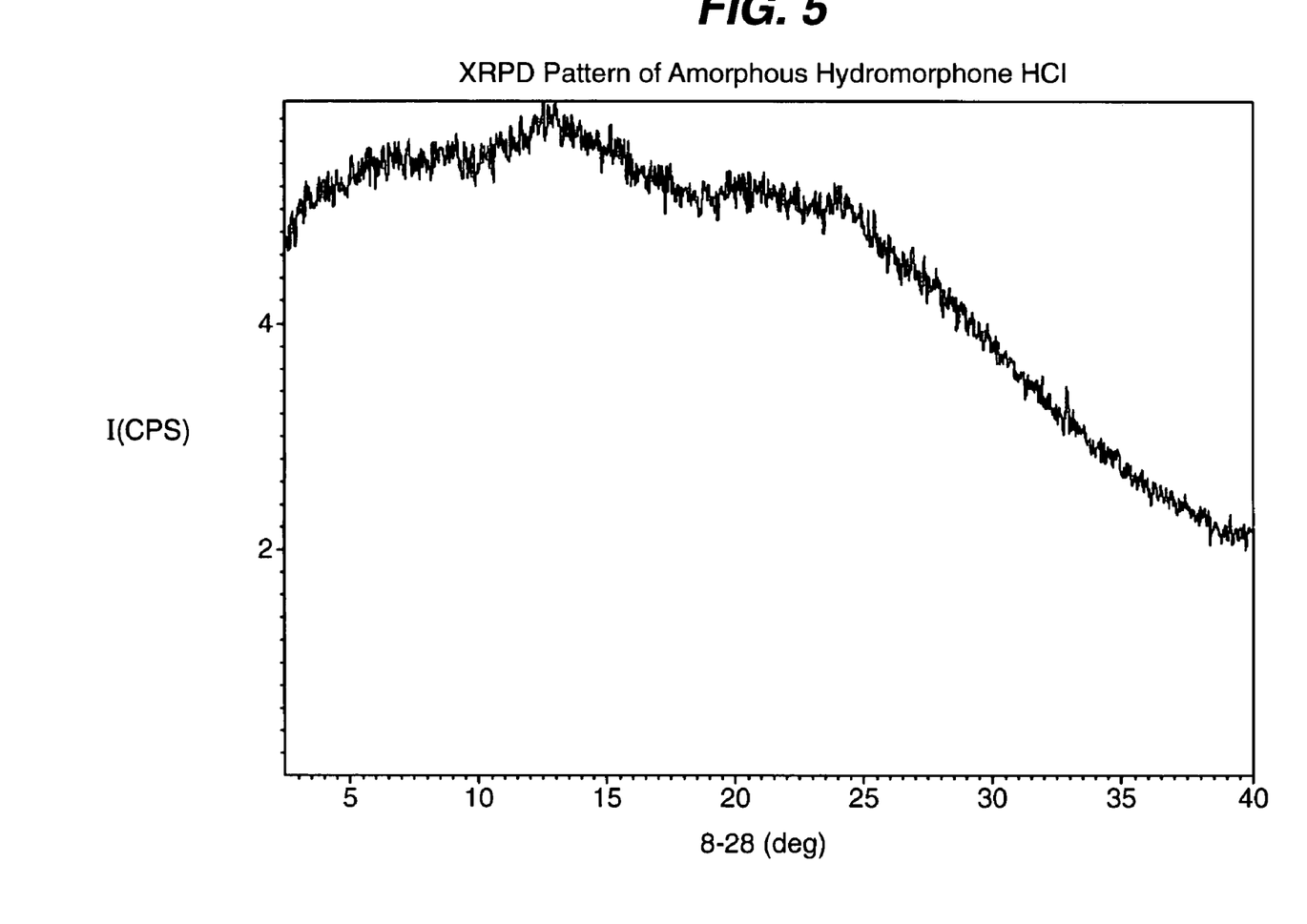
FIG. 5 is an X-ray powder diffraction pattern of hydromorphone HCl, amorphous form expressed in terms of °2θ.

The data for the known form of hydromorphone HCl Form A as-received from Noramco Inc. (Wilmington, Del.) was generated using a Shimadzu XRD-6000 X-ray powder diffractometer using Cu Kα radiation, fitted with a long fine-focus X-ray tube, set at a tube voltage of 40 kV and amperage of 40 mA. The divergence and scattering slits were set at 1° and the receiving slit was set at 0.3 mm. Diffracted radiation was detected by a NaI scintillation detector. A theta-two theta continuous scan at 2.4°/min (1 sec/0.04° step) from 2.5 to 40 °2θ was used. The sample was rotated at 60 rotations per minute during analysis. A silicon standard was analyzed to check the instrument alignment. Data were collected and analyzed using XRD-6000 v. 4.1. Sample was prepared for analysis using an aluminum backfill holder.

The data for samples of Forms B, C, D and the amorphous form of hydromorphone HCl made according to the Examples which follow were generated using an Inel XRG-3000 diffractometer equipped with a CPS (Curved Position Sensitive) detector with a 2θ range of 120°. Real time data were collected using Cu-Kα radiation starting at approximately 4 °2θ at a resolution of 0.03 °2θ. The tube voltage and amperage were set to 40 kV and 30 mA, respectively. The monochromator slit was set at 5 mm by 80 μm or 160 μm. The pattern is displayed from 2.5-40 °2θ. Samples were prepared for analysis by packing them into thin-walled glass capillaries. Each capillary was mounted onto a goniometer head that is motorized to permit spinning of the capillary during data acquisition. The samples were analyzed for 5 or 10 min. Instrument calibration was performed using a silicon reference standard.

TABLE I

Crystalline Hydromorphone HCl XRPD Peak (°2θ) and Relative Intensities

| Form A | | Form B | | Form C | | Form D | | amorphous |
|---|---|---|---|---|---|---|---|---|
| °2θ | I/Io | °2θ | I/Io | °2θ | I/Io | °2θ | I/Io | °2θ |
| 9.22 | 11 | 8.40 | 48 | 8.53 | 44 | 8.43 | 60 | broad halo, |
| 13.28 | 79 | 8.95 | 21 | 9.24 | 29 | 9.04 | 24 | no specific |
| 14.54 | 88 | 11.88 | 62 | 12.19 | 42 | 11.98 | 83 | peaks |
| 14.86 | 37 | 12.17 | 13 | 12.48 | 100 | 12.43 | 100 | present |
| 15.74 | 56 | 12.44 | 100 | 15.82 | 11 | 13.09 | 8 | |

TABLE I-continued

Crystalline Hydromorphone HCl XRPD Peak (°2θ) and Relative Intensities

| Form A | | Form B | | Form C | | Form D | | amorphous |
|---|---|---|---|---|---|---|---|---|
| °2θ | I/Io | °2θ | I/Io | °2θ | I/Io | °2θ | I/Io | °2θ |
| 17.39 | 34 | 13.02 | 8 | 16.11 | 16 | 15.64 | 9 | |
| 18.58 | 16 | 14.98 | 6 | 17.01 | 16 | 15.93 | 29 | |
| 19.40 | 80 | 15.55 | 6 | 17.37 | 7 | 16.87 | 11 | |
| 20.01 | 65 | 15.85 | 35 | 17.62 | 9 | 17.22 | 30 | |
| 21.35 | 88 | 17.00 | 35 | 18.06 | 13 | 17.78 | 18 | |
| 22.53 | 31 | 17.66 | 14 | 18.39 | 36 | 18.18 | 22 | |
| 22.99 | 9 | 18.12 | 21 | 19.11 | 56 | 18.85 | 48 | |
| 23.26 | 7 | 18.48 | 15 | 19.53 | 15 | 19.35 | 66 | |
| 23.73 | 9 | 18.73 | 48 | 19.72 | 15 | 19.67 | 15 | |
| 24.38 | 28 | 19.23 | 36 | 20.09 | 15 | 20.09 | 13 | |
| 24.95 | 85 | 19.99 | 10 | 23.46 | 7 | 20.87 | 6 | |
| 25.95 | 100 | 24.23 | 41 | 24.57 | 16 | 24.40 | 83 | |
| 27.05 | 8 | 24.64 | 8 | 24.75 | 26 | 24.94 | 18 | |
| 27.60 | 12 | 24.95 | 20 | 25.02 | 13 | 25.29 | 33 | |
| 29.07 | 22 | 25.14 | 32 | 25.64 | 23 | 25.84 | 18 | |
| 30.93 | 8 | 25.71 | 9 | 26.14 | 12 | 26.34 | 12 | |
| 31.58 | 8 | 26.60 | 11 | 26.91 | 16 | 26.71 | 9 | |
| 31.94 | 7 | 27.17 | 16 | 28.12 | 9 | 26.91 | 7 | |
| 32.66 | 72 | 27.53 | 14 | 28.48 | 10 | 27.50 | 29 | |
| 33.62 | 11 | 28.19 | 10 | 33.74 | 13 | 28.29 | 12 | |
| 35.31 | 18 | 28.93 | 9 | | | 29.17 | 9 | |
| 36.14 | 20 | 29.75 | 6 | | | 29.56 | 7 | |
| 36.82 | 12 | | | | | 32.22 | 7 | |
| 37.78 | 14 | | | | | 32.81 | 6 | |
| 38.13 | 18 | | | | | 33.39 | 12 | |
| 39.26 | 11 | | | | | | | |

Table II summarizes the peaks of the XPRD patterns of each hydromorphone HCl form that uniquely define each form.

TABLE II

Unique XRPD Peaks for Hydromorphone HCl

| Form A °2θ | Form B °2θ | Form C °2θ | Form D °2θ |
|---|---|---|---|
| 14.54 | 11.88 | 9.24 | 17.22 |
| 21.35 | 27.17 | 12.48 | 18.85 |
| | | 19.11 | |

The forms of the invention may be further defined by other physical properties such as those in Table III.

Differential scanning calorimetry ("DSC") was performed using a TA Instruments differential scanning calorimeter 2920. The sample was placed into an aluminum DSC pan, and the weight accurately recorded. The pan was covered with a lid and then crimped. The sample cell was equilibrated at ambient temperature and heated under a nitrogen purge at a rate of 10° C./min, up to a final temperature of 375° C. Indium metal was used as the calibration standard. Reported temperatures are at the transition maxima.

The DSC analysis of amorphous hydromorphone hydrochloride was performed as described above, except that a heating rate of 30° C./min was used, and the sample was analyzed from −40° C. up to 375° C.

Thermogravimetric analyses ("TGA") were performed using a TA Instruments 2950 thermogravimetric analyzer. The sample was placed in an aluminum sample pan and inserted into the TG furnace. The sample was first equilibrated at 25° C., then heated under nitrogen at a rate of 10° C./min, up to a final temperature of 375° C. Nickel and Alumel™ were used as the calibration standards.

TABLE III

Unique Thermal Properties of Hydromorphone HCl Polymorphs

| Form | Analysis[a] | Unique Properties |
|---|---|---|
| A | DSC* | 328° C. endotherm maximum |
| | TGA** | 0.1% wt. loss from 25-200° C. |
| B | DSC | endotherms: peak max$_1$ = 70° C. (shoulder), peak max$_2$ = 84° C., peak max$_3$ = 333° C. |
| | TGA | 2.4% wt. loss from 25-106° C., 1% wt. loss from 106-241° C. |
| C | DSC | endotherms: peak max$_1$ = 126° C. (broad), peak max$_2$ = 230° C. (shoulder), peak max$_3$ = 330° C. |
| | TGA | 2% wt. loss from 25-83° C., 1% wt. loss from 83-219° C. |
| D | DSC | 329° C. endotherm maximum |
| | TGA | 1% wt. loss from 25-212° C. |
| amorphous | DSC | endotherms: peak max$_1$ = 100° C. (broad shoulder peak), peak max$_2$ = 118° C., peak max$_3$ = 347° C. |

*Differential scanning calorimetry;
**TGA = thermogravimetric analysis

As used herein the term "hydromorphone hydrochloride" or "hydromorphone HCl" when used alone and without modifiers, refers to the known form or Form A of hydromorphone hydrochloride.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of providing an analgesic effect described in the present invention may also be carried out using a pharmaceutical composition comprising any of the compounds as defined herein and a pharmaceutically acceptable carrier. The pharmaceutical composition may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

The invention is further defined by reference to the following examples, which are intended to be illustrative and not limiting. The novel forms of the present invention were made according to the processes of Examples 1-9. The processes of Examples 10-15 did not provide novel forms of hydromorphone HCl, but merely resulted in the recovery of the known form, hydromorphone HCl Form A.

EXAMPLE 1

Preparation of Form B 55 mg of hydromorphone HCl was dissolved in 0.2 ml of water. The solution was filtered through a 0.2 μm nylon syringe filter into a clean vial. The vial was covered with Parafilm perforated with pinholes and placed in a fume hood for slow evaporation at ambient conditions to afford the title form.

EXAMPLE 2

Preparation of Form B 56 mg of amorphous hydromorphone HCl as prepared in Example 9 was weighed into a vial. The vial was placed uncapped within a 94% RH (relative humidity) jar at ambient temperature for about 1.5 hours to afford the title form.

EXAMPLE 3

Preparation of Form B 63 mg of hydromorphone HCl was dissolved in 1 ml of tetrahydrofuran-water (4:1) mixture. The solution was filtered through a 0.2 μm nylon syringe filter into a clean vial. The vial was covered with Parafilm perforated with pinholes and placed in a fume hood for slow evaporation at ambient conditions. The resulting yellow gel was then slurried in 0.4 ml of tert-butyl methyl ether at 50° C. The resulting solid sample was retrieved by decanting the solution and drying the solids at ambient conditions to provide the title form.

EXAMPLE 4

Preparation of Form B 57 mg of hydromorphone HCl was dissolved in 1 ml of an ethanol-water (4:1) mixture. The solution was filtered through a 0.2 μm nylon syringe filter into a clean vial. The vial was covered with Parafilm perforated with pinholes and placed in a fume hood for slow evaporation at ambient conditions. The resulting gel sample was then placed uncovered within a larger vial containing 3 ml of ethyl acetate. The larger vial was capped, sealed with Parafilm, and stored at ambient to provide the title form.

EXAMPLE 5

Preparation of Form C 91 mg of hydromorphone HCl was dissolved in 0.4 ml of acetonitrile-water (1:1) mixture. The solution was filtered through a 0.2 µm nylon syringe filter into a clean vial. The vial was placed uncapped in a 61° C. oven for fast evaporation to afford the title form.

EXAMPLE 6

Preparation of Form D 103 mg of hydromorphone HCl was dissolved in 1.2 ml of acetone-water (2:1) mixture. The solution was filtered through a 0.2 µm nylon syringe filter into a clean vial. The vial was covered with Parafilm perforated with pinholes and placed in a fume hood for slow evaporation at ambient conditions to provide the title form.

EXAMPLE 7

Preparation of Form D 67 mg of hydromorphone HCl was dissolved in 1.2 ml of ethanol-water-methanol (4:1:1) mixture. The solution was filtered through a 0.2 µm nylon syringe filter into a clean vial. The vial was covered with Parafilm perforated with pinholes and placed in a fume hood for slow evaporation at ambient conditions to provide the title form.

EXAMPLE 8

Preparation of Form D 50 mg of hydromorphone HCl was dissolved in 0.2 ml of water. The solution was filtered through a 0.2 µm nylon syringe filter into a clean vial, which was placed uncapped within a 20-ml vial containing 3 ml of 1,4-dioxane. The 20-ml vial was capped and stored at ambient temperature. After 13 days, the sample was allowed to fast evaporate by placing the sample vial uncapped at ambient temperature to afford the title form.

EXAMPLE 9

Preparation of Amorphous Form 119 mg of hydromorphone HCl was dissolved in 50 ml of water. The resulting solution was filtered through a 0.2 µm nylon syringe filter into a 250 ml round bottom flask. The flask was immersed and rotated at an angle in a isopropanol-dry ice bath to form a thin layer of frozen hydromorphone HCl solution around the inside wall of the flask. The frozen solution was evaporated under reduced pressure using a freeze dryer (Flexi-Dry, FTS systems) at −50° C. for about 24 hours. The resulting solids were stored in dessicator to afford the title form.

EXAMPLE 10

Form A 66 mg of hydromorphone HCl was dissolved in 1.7 ml of 1-butanol-water-methanol (5:1:1) mixture. The solution was filtered through a 0.2 µm nylon syringe filter into a clean vial. The vial was left uncovered in a fume hood under ambient conditions for fast evaporation. The resulting wet solids were dried under nitrogen stream before analysis to provide the title form.

Other solvent or solvent mixtures such as acetone-water (7:1), acetonitrile-water (15:2), dichloromethane-2,2,2-trifluoroethanol, 1,4-dioxane-water (15:2), ethanol-water (7:1), methanol-water (3:1), tetrahydrofuran-water (7:1), and 2,2,2-trifluoroethanol were used in this method and yielded the same crystalline form, Form A.

EXAMPLE 11

Form A 51 mg of hydromorphone HCl was dissolved in 0.75 ml of isopropanol-water-methanol (3:1:1) mixture. The solution was filtered through a 0.2 µm nylon syringe filter into a clean vial. The vial was covered with Parafilm perforated with pinholes and placed in a fume hood for slow evaporation at ambient conditions to afford the title form.

Other solvent and solvent mixtures such as 2,2,2-trifluoroethanol and 1-propanol-water-methanol (5:1:1) were used in this method and yielded the same crystalline form, Form A.

EXAMPLE 12

Form A 92 mg of hydromorphone HCl was slurried in 0.4 ml of methanol-water (3:1) mixture at 62° C. for 5 days. The solution was filtered while warm through a 0.2 µm nylon syringe filter into a clean vial immersed in a water bath at 60° C. Heat source to the water bath was turned off to slowly cool the sample to ambient temperature. The sample was later placed in a refrigerator and then a freezer. The resulting solid sample was retrieved by decanting the solution and then drying the sample briefly under nitrogen stream

EXAMPLE 13

Form A 124 mg of hydromorphone HCl was slurried in 0.4 ml of 2,2,2-trifluoroethanol at 51° C. for a day. The slurry was filtered while warm through a 0.2 µm nylon syringe filter into a clean vial containing 1 ml of isopropyl acetate. The resulting solid precipitates were collected by vacuum filtration to afford the title form.

EXAMPLE 14

Form A 46 mg of hydromorphone HCl was dissolved in 0.3 ml of 2,2,2-trifluoroethanol. The resulting solution was filtered through a 0.2 µm nylon syringe filter into a clean vial, which was placed uncapped within a larger vial containing 3 ml of isopropyl acetate. The larger vial was capped, sealed with Parafilm, and stored at ambient temperature. The resulting solid sample was retrieved by decanting the solution and then drying the sample briefly under nitrogen stream to afford the title form.

Other samples using this same method were prepared in the same solvent (2,2,2-trifluoroethanol) but with varying diffusing antisolvents, such as 1,4-dioxane, nitromethane, and tert-butyl methyl ether. The same method was also used by using water as the solvent and acetonitrile as the diffusing antisolvent. All these setups yielded the same crystalline form A.

EXAMPLE 15

Form A 10 mg of hydromorphone HCl was dissolved in 0.16 ml of 2,2,2-trifluoroethanol-nitromethane (3:1) mixture. The resulting solution was filtered through a 0.2 µm nylon syringe filter. About 30 µL of the sample solution was then filled into a 1.0 mm glass capillary. The capillary sample was evaporated in a 60° C. oven to provide the title form.

What is claimed is:

1. Form B of hydromorphone hydrochloride having XRPD °2θ peaks at about 8.40, 8.95, 11.88, 12.17, 12.44, 13.02, 14.98, 15.55, 15.85, 17.00, 17.66, 18.12, 18.48, 18.73, 19.23, 19.99, 24.23, 24.64, 24.95, 25.14, 25.71, 26.60, 27.17, 27.53, 28.19, 28.93 and 29.75.

2. Form C of hydromorphone hydrochloride having XRPD °2θ peaks at about 8.53, 9.24, 12.19, 12.48, 15.82, 16.11, 17.01, 17.37, 17.62, 18.06, 18.39, 19.11, 19.53, 19.72, 20.09, 23.46, 24.57, 24.75, 25.02, 25.64, 26.14, 26.91, 28.12, 28.48 and 33.74.

3. Form D of hydromorphone hydrochloride having XRPD °2θ peaks at about 8.43, 9.04, 11.98, 12.43, 13.09, 15.64, 15.93, 16.87, 17.22, 17.78, 18.18, 18.85, 19.35, 19.67, 20.09, 20.87, 24.40, 24.94, 25.29, 25.84, 26.34, 26.71, 26.91, 27.50, 28.29, 29.17, 29.56, 32.22, 32.81 and 33.39.

4. The amorphous form of hydromorphone hydrochloride having no specific XRPD °2θ peaks and having a DSC thermogram comprising endotherm transitions at about 100° C., about 118° C. and about 347° C.

5. Form B of hydromorphone hydrochloride, having XRPD °2θ peaks at about 11.88 and 27.17.

6. Form C of hydromorphone hydrochloride, having XRPD °2θ peaks at about 9.24, 12.48 and 19.11.

7. Form D of hydromorphone hydrochloride, having XRPD °2θ peaks at about 17.22 and 18.85.

8. A form of claim 1, 2 or 3 which is 90-100% pure (wt./wt.).

9. A form of claim 8 that is 95-100% pure.

10. A form of claim 9 that is 98-100% pure.

11. A process for making hydromorphone hydrochloride Form B, which comprises: dissolving hydromorphone hydrochloride in a solvent selected from water or 4:1 (v/v) tetrahydrofuran:water mix, filtering the solution, and evaporating to dryness under ambient conditions to yield the Form B.

12. A process for making hydromorphone hydrochloride Form C, which comprises: dissolving hydromorphone hydrochloride in acetonitrile:water mix, filtering the solution and evaporating to dryness at an elevated termperature to yield the Form C.

13. A process for making hydromorphone hydrochloride Form D, which comprises: dissolving hydromorphone hydrochloride in a solvent selected from water, ethanol:water:methanol mix or acetone:water mix, filtering the solution, and evaporating to dryness under ambient conditions to yield the Form D.

14. A process for making an amorphous form of hydromorphone hydrochloride, which comprises: dissolving hydromorphone hydrochloride in water, filtering the solution and evaporating to dryness under reduced temperature and reduced pressure to yield the amorphous form.

15. A form of claim 5, 6 or 7 which is 90-100% pure (wt./wt.).

16. A form of claim 15 that is 95-100% pure.

17. A form of claim 16 that is 98-100% pure.

* * * * *